United States Patent [19]

Kojima et al.

[11] Patent Number: 4,477,487
[45] Date of Patent: Oct. 16, 1984

[54] METHOD OF PRODUCING OXYGEN CONCENTRATION CELLS

[75] Inventors: Takao Kojima, Nagoya; Naoto Naganuma, Seki, both of Japan

[73] Assignee: NGK Spark Plug Co., Ltd., Nagoya, Japan

[21] Appl. No.: 469,828

[22] Filed: Feb. 25, 1983

Related U.S. Application Data

[63] Continuation of Ser. No. 262,643, May 11, 1981, abandoned.

[30] Foreign Application Priority Data

May 14, 1980 [JP] Japan .................................. 55-63679

[51] Int. Cl.³ ............................................. G01N 27/58
[52] U.S. Cl. .................................... 427/123; 427/125;
427/126.3; 427/180; 427/190; 427/201;
427/376.2; 427/383.3; 427/383.5; 427/404;
427/419.2; 204/429
[58] Field of Search ..................... 427/125, 126.3, 180,
427/190, 201, 376.2, 383.3, 383.5, 404, 419.2,
423, 123; 204/429

[56] References Cited

U.S. PATENT DOCUMENTS

| | | | |
|---|---|---|---|
| 3,617,358 | 9/1967 | Dittrich | 427/423 |
| 3,640,757 | 2/1972 | Grubba | 427/34 |
| 4,170,530 | 10/1979 | Watanabe et al. | 204/195 |
| 4,170,531 | 10/1979 | Watanabe et al. | 427/125 |
| 4,253,934 | 3/1981 | Berg et al. | 204/424 |
| 4,257,863 | 3/1981 | Hoffman | 427/125 |
| 4,280,890 | 7/1981 | Friese et al. | 427/125 |
| 4,359,374 | 11/1982 | Sano et al. | 204/429 |

FOREIGN PATENT DOCUMENTS

53-12392  2/1978  Japan .
53-29187  3/1978  Japan .
53-78885  7/1978  Japan .

*Primary Examiner*—Norman Morgenstern
*Assistant Examiner*—Richard Bueker
*Attorney, Agent, or Firm*—Fleit, Jacobson, Cohn & Price

[57] ABSTRACT

An oxygen concentration cell having a high peeling resistance of the electrode and an excellent response property can be obtained by a method wherein electrode-adhering particles, which consist essentially of a specifically limited amount of stabilized or partially stabilized zirconia granulated particles having a spherical shape and a particle size of not smaller than 44 μm and a specifically limited amount of stabilized or partially stabilized zirconia fine particles having a particle size of not larger than 10 μm as a sintering aid, are applied and adhered to the surface of a matrix consisting of stabilized or partially stabilized zirconia, the resulting assembly is sintered to form monolithically a large number of convex portions on the matrix surface, an electrode is adhered to the matrix surface having the convex portions monolithically formed thereon, and further a heat-resistant ceramic protecting film is adhered to the electrode film.

6 Claims, 2 Drawing Figures

METHOD OF PRODUCING OXYGEN CONCENTRATION CELLS

This is a continuation of application Ser. No. 262,643 filed May 11, 1981, now abandoned.

BACKGROUND OF THE INVENTION (1) Field of the Invention

The present invention relates to an improved method of producing oxygen concentration cells, and more particularly relates to a novel method of forming an electrode of oxygen concentration cell.

(2) Description of the Prior Art

It has been known that an oxygen concentration cell, which operates by utilizing the oxygen ion-conductivity of solid electrolyte, is used as a sensor for detecting the presence or absence of oxygen. When the oxygen concentration cell is used as the above described sensor, the electrode is required not to be peeled off even when the electrode is exposed for a long period of time to a high temperature gas to be detected. In order to satisfy this demand, there have hitherto been proposed various methods, for example, (a) a method wherein a sintered oxygen ion-conductive solid electrolyte matrix is subjected to acid etching, sandblasting or the like to form a rough surface; (b) a method wherein a porous film consisting of the same material as that of a detecting element is formed on the surface of the detecting element (Japanese Patent Laid Open Application No. 12,392/78); (c) a method wherein a porous film is formed on the surface of a sintered detecting element (Japanese Patent Laid Open Application No. 29,187/78); (d) a method wherein a substance consisting of the same material as that of a detecting element is flame-sprayed by means of a plasma spray on the surface of a sintered detecting element to form a porous film thereon (Japanese Patent Laid Open Application No. 78,885/78); and the like.

However, these methods have the following drawbacks, and are still insufficient for practical use. That is, in the method (a), the mechanical and thermal strength of the matrix are noticeably deteriorated, and the matrix cracks often during the use. In the method (b), relatively fine particles (not larger than 20 $\mu$m) after pulverizing step are directly adhered to the matrix to form a porous film on the matrix surface, and therefore the electrode is apt to peel together with the porous film during the use. The reason is probably as follows. Since the electrode is penetrated into the voids of the porous film, the electrode has a somewhat long duration time, but when the electrode is exposed to a reducing atmosphere, the electrode is sintered to cause growth and change of properties of particles and to cause a high mechanical stress in the porous portion of the film, and moreover the porous film is very weak against mechanical stress due to its porous structure, and hence the porous film cracks, and peels together with the electrode. In the method (c), a slurry is applied to the surface of a previously sintered detecting element and the assembly is sintered to form a porous film. Therefore, the porous film is not firmly bonded to the matrix, and the porous film is apt to peel easily during the use. In the method (d), the reaction between the sprayed substance and the sintered detecting element is weak, and the sprayed substance peels together with the electrode. In order to prevent this drawback, when the plasma spraying is carried out at a high temperature, a thermal gradient is caused in the detecting element matrix, and the matrix is apt to crack easily. While, when the plasma spraying is carried out at room temperature, and then the resulting assembly is sintered, the thermal gradient does not occur in the matrix, but the procedure is troublesome.

SUMMARY OF THE INVENTION

The object of the present invention is to provide a method of producing oxygen concentration cells, which do not have the above described drawbacks of conventional cells and have a remarkably excellent peeling resistance of the electrode.

The essential feature of the present invention consists in a method of producing oxygen concentration cells exposed to high temperature combustion gas, comprising applying and adhering to the surface of a matrix formed by press molding stabilized or partially stabilized zirconia raw material powders, electrode-adhering particles, which consist essentially of stabilized or partially stabilized zirconia granulated particles having a spherical shape and stabilized or partially stabilized zirconia fine particles having a particle size of not larger than 10 $\mu$m as a sintering aid, and contain not less than 50% by weight of the granulated particles, provided that the particle size is not smaller than 44 $\mu$m, and not less than 10% by weight of the fine particles; sintering the assembly to form monolithically a large number of convex portions on the surface of the press molded matrix; adhering an electrode to the matrix surface having the convex portions monolithically formed thereon; and further adhering a protecting film consisting of a heat-resistance ceramic material to the electrode film.

DESCRIPTION OF THE PREFERRED EMBODIMENT

Figure 1:
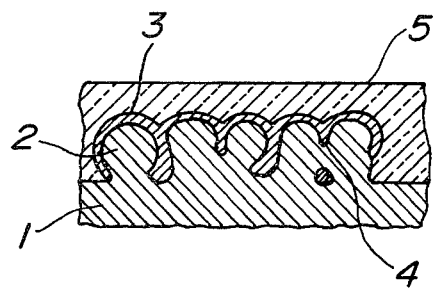
FIG. 1 is an enlarged cross-sectional view of the essential part of an oxygen concentration cell produced according to the method of the present invention.
Figure 2:
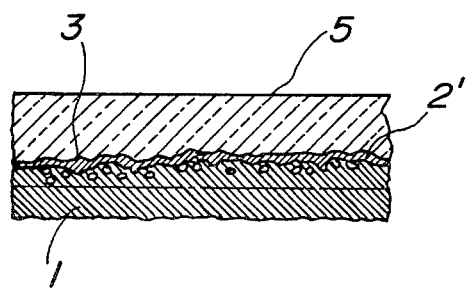
FIG. 2 is an enlarged cross-sectional view of the essential part of an oxygen concentration cell produced by a method outside the scope of the present invention.

The present invention will be explained in more detail hereinafter. The ion-conductive solid electrolyte to be used in the present invention is produced in the following manner. $ZrO_2$ is mixed with a metal oxide, such as CaO, $Y_2O_3$, MgO or the like, in a given mixing ratio, the resulting mixture is pulverized and then calcined in an electric furnace. The calcined powders are again pulverized to produce stabilized or partially stabilized zirconia raw material powders. The zirconia raw material powders are press molded into a given shape, for example, to a cylindrical body closed at its one end, which is used as a matrix. The present invention is characterized in that such a green matrix is adhered with electrode-adhering particles consisting of stabilized or partially stabilized zirconia granulated particles, which are obtained by granulating fine primary particles, and more than half of which are occupied by particles having a particle size of not smaller than 44 $\mu$m (not passable through 350 mesh sieve), and stabilized or partially stabilized zirconia fine particles having a particle size of not larger than 10 $\mu$m as a sintering aid, and containing not less than 50% by weight of the above described granulated particles, provided that the particle size is not smaller than 44 μm, and not less than 10% by weight of the fine particles based on the total amount of the electrode-adhering particles. Then, the above obtained assembly of the press-molded matrix and electrode-adhering particles adhered thereto is sintered to produce the ion-conductive solid electrolyte. As the result, in the ion-conductive solid electrolyte, a part of the electrode adhering particles are firmly bonded with the matrix to form convex portions 2 projected from the matrix 1 as illustrated in FIG. 1. When an electrode 3 is adhered to the matrix surface having convex portions 2 projected therefrom, the electrode 3 penetrates into the concave portions 4 formed between the convex portions 2 and adhered thereto to form a large surface area of the electrode. Furthermore, the electrode 3 penetrates into the gaps formed between the convex portions of the surface of the matrix 1 itself, and is firmly bonded to the matrix 1 through the convex portions. On the contrary, when particles having a size of smaller than 44 μm, for example, particles having a size of up to about 10 μm, are adhered to the matrix, and the assembly is sintered, a so-called porous film containing very small holes or very small concave portions formed complicatedly between very small convex portions 2′ is formed as illustrated in FIG. 2. Even when an electrode 3 is adhered to the matrix surface having such convex portions 2′, the electrode can not be adhered to the interior portion of the concave portions, and peels easily during the use due to the reason as described above.

In the present invention, granulated particles are used based on the reason that the granulated particles have a very high sinterability. As disclosed in the above described Japanese Patent Laid Open Application No. 29,187/78, particles produced by pulverizing calcined powders have poor sinterability even when they have a particle size of not smaller than 44 μm, and moreover since the particles do not have a spherical shape, uniform convex portions are difficult to be formed on the matrix surface, and the adhesion strength of the resulting convex portions to the matrix is poor and unstable. Among the granulated particles, particles produced through granulation by means of a spray drier have an excellent bonding property with the matrix and are preferably used. The reason is that the particles have a stable and uniform shape and are dense.

In the present invention, fine particles having a particle size of not larger than 10 μm, preferably not larger than several μm, act as an sintering aid, and serves to bond advantageously the granulated particles having a particle size of not smaller than 44 μm to the matrix. Fine particles having a size of larger than 10 μm are poor as sintering aids.

Fine particles having a size of not larger than 10 μm, used as a sintering aid, may be contained in the electrode-adhering particles in an amount of up to 50% by weight. When electrode-adhering particles contain more than 50% by weight of the fine particles, the above described effect of the granulated particles having a size of not smaller than 44 μm lowers. When electrode-adhering particles contain the granulated particles having size of not smaller than 44 μm and the fine particles having a size of not larger than 10 μm in a ratio of the former particle of 60~80% to the latter particle of 40~20%, the electrode-adhering particles exhibit particularly excellent bonding force. When granulated particles are produced from a raw material mixture of zirconia raw material powders with up to 5% of a sintering aid based on the amount of the zirconia raw material powders, it is preferable to use smaller amount of fine particles as a sintering aid. In this case, as the sintering aid, there can be used $Al_2O_3$, $SiO_2$, $Fe_2O_3$ and the like. Among them, $Fe_2O_3$ is particularly excellent.

The above described electrode-adhering particles are mixed with a proper amount of a proper binder to be made into fluid, and then applied and adhered to a matrix by means of a brush or the like. However, it has been found that the electrode-adhering particles can be adhered to the matrix by adhering firstly the granulated particles to the matrix surface and then adhering the fine particles to the layer of the granulated particles. When the adhesion treatment of the electrode-adhering particles to the matrix surface is carried out such that the granulated particles are applied and adhered to the matrix surface in the form of one larger or in the form of at must several layers, the object of adhering the electrode-adhering particles to the matrix surface can be attained. After the matrix surface is adhered with the electrode-adhering particles, the assembly is fully dried and then sintered at 1,500°~1,700° C. for 1~3 hours under an oxidizing atmosphere, whereby the electrode-adhering particles and the matrix are formed into a monolith structure, wherein a large number of convex portions are formed on the matrix surface. Then, a heat-resistant catalytic metal is adhered to the matrix surface having convex portions formed thereon by means of the thin film technique to form an electrode. As the heat-resistant catalytic metal, use is made of platinum, ruthenium, rhodium, palladium, gold, silver and alloys thereof. As the thin film technique, there can be used not only conventional thin film techniques, such as vacuum deposition, chemical deposition and the like, but also electroless plating, electrolytic plating, and a method wherein a salt of electrode-forming metal is applied to the matrix surface having convex portions formed thereon and then the assembly is heated to decompose the metal salt and to deposit the metal on the matrix surface. Among the above described techniques, plating method is advantageously carried out in view of productivity. Then, a ceramic protecting film 5 is adhered to the metal film as illustrated in FIG. 1 by means of a plasma spray coating or the like.

The above described method discloses a method of forming the outside electrode, which is exposed to the gas to be detected. The inside electrode can be formed by a method other than the above described method, and can be formed on the inner surface of the matrix by the above described thin film technique. Among the thin film techniques, a plating method, particularly a method wherein a platinum group metal is plated on the surface of a solid electrolyte by an electroless plating under a condition for forming active points of the platinum group metal on the solid electrolyte surface, and then an electroless plating is again carried out, and then the assembly is heat treated at a temperature lower than the sintering temperature of the solid electrolyte, is preferable in view of the productivity and the uniform porosity of the resulting oxygen concentration cell.

In the above described method of producing an oxygen concentration cell of the present invention, green granulated particles are adhered to an unsintered matrix, that is, to a green matrix, by the aid of fine particles having a size of not larger than 10 μm. Therefore, the matrix and the electrode-adhering particles are firmly bonded with each other, and they do not peel from each other during the use. Moreover, the electrode-adhering particles contain predominantly spherical particles having a size of not smaller than 44 μm, and therefore the surface of the sintered matrix has large and uniform projections formed thereon, and the electrode to be adhered to the uneven surface penetrates into the interior of the gaps formed between the projections, and the penetrated electrode acts as a wedge to prevent the peeling of the electrode itself. Moreover, a sufficiently large three-phase boundary surface is formed, and the oxygen concentration cell of the present invention has a sufficiently excellent response property.

The following example is given for the purpose of illustration of this invention and is not intended as a limitation thereof.

EXAMPLE 1

(Step 1):

Zirconium oxide as a raw material was mixed with 4~12 mol%, based on the amount of the zirconium oxide, of fine powders of yttrium oxide, and the resulting mixture was pulverized in wet state for 70 hours to obtain particles having a size of not larger than 10 μm. The particles were dried over one night, and then passed through a 20 mesh sieve.

(Step 2):

The above treated particles were calcined at 1,300° C. for 1 hour in an electric furnace and then passed through a 20 mesh sieve.

(Step 3):

The particles obtained in Step 2 were pulverized for 50 hours in wet state together with an organic binder, and then granulated by means of a spray drier such that the resulting granulated particles contained 95% by weight of particles having a size of not smaller than 44 μm (not passable through 350 mesh sieve) and contained 90% by weight of particles having a size of not larger than 150 μm and had an average particle size of 75 μm. The granulated particles consisted of stabilized or partially stabilized zirconia having a purity of 93%.

(Step 4):

The water content of the granulated particles obtained in Step 3 was adjusted to 1%, and then the granulated particles were subjected to a rubber press molding under a pressure of 50 MPa, and the molded article was cut so as to obtain a cylindrical body closed at its one end, which was used as a matrix.

(Step 5):

As the granulated particles to be used in the electrode-adhering particles, the following granulated particles were produced.

Granulated particles (1): granulated particles obtained in Step 3.

Granulated particles (2): granulated particles which remained on a 325 mesh (44 μm) sieve when granulated particle (1) were sieved by the 325 mesh sieve.

Granulated particles (3): granulated particles obtained from the zirconium oxide used in Step 1 through a procedure, wherein the zirconium oxide is mixed with not more than 5% by weight of an impurity of $Al_2O_3$, $SiO_2$, $Fe_2O_3$ or the like, and the resulting mixture was subjected to the treatments of Steps 2 and 3 successively, and then the resulting granulated particles were sieved by a 350 mesh (44 μm) sieve, and particles which remained on the 350 mesh (44 μm) sieve were gathered.

Granulated particles (4): A mixture of granulated particles (2) with particles passed through the 350 mesh sieve in the production of granulated particles (2), which mixture has an average particle size within the range of 50~100 μm.

(Step 6):

Particles of raw material obtained in Step 2 were further pulverized to obtain fine particles having a size of not larger than 10 μm (particles not larger than 10 μm: 100% and particles not larger than 2.5 μm: 88%).

Each of the granulated particles (1)~(4) produced in the above Step 5 was mixed with the above obtained fine particles such that the resulting electrode-adhering particles had a composition shown in the following Table 1 and the electrode-adhering particles were added with a binder consisting of sodium celluloseglycolate to produce fluidized and adherent electrode-adhering particles.

(Step 7):

The electrode-adhering particles produced in Step 6 were applied and adhered to the matrix produced in Step 4 in a thickness of within the range of 40~300 μm by means of a brush.

(Step 8):

The resulting assembly in Step 7 was fully dried, and then sintered at 1,550°~1,700° C. for 1 hour in a chamber kept under an oxidizing gas atmosphere.

(Step 9):

After the surface of the sintered body obtained in Step 7 was fully washed by an ultrasonic cleaning, the surface was activated by chloroplatinic acid, and then subjected to an electroless plating, followed by an electrolytic plating. Then, the above treated mass was heat treated at 1,300° C. to form porous platinum electrode having relatively large holes.

(Step 10):

A protecting film consisting of spinel and having a thickness of about 100 μm was formed on the electrode surface by means of a flame spraying method.

(Step 11):

The inner surface of the tubular matrix was activated by chloroplatinic acid, and the activated inner surface was subjected to an electroless plating and then to a heat treatment at 700° C. to obtain porous platinum electrode having a relatively small holes.

The above obtained detecting element was subjected to the following peeling test. That is, a treatment, wherein the tip portion of the element was heated from 350° C. up to 930° C. in about 10 minutes under an reducing atmosphere of Bunsen burner, and then cooled naturally in air from 930° C. to 350° C. in about 5 minutes, was used as one cycle, and this cycle was continued for more than about 500 hours to effect the durability test of the detecting element, and the time required for peeling the electrode from the solid electrolyte after the beginning of the test was measured. The obtained results are shown in Table 1. Further, when detecting elements have a durability of longer than 500 hours were actually fitted to the exhaust pipe of engine, and the performance of the elements was measured, the elements had a high performance enough to be used practically.

TABLE 1

| Sample No. | Fine particles used as a sintering aid (not larger than 10 μm) | Granulated particles Particle size: smaller than 44 μm | Granulated particles Particle size: not smaller than 44 μm | Remarks | Peeling resistance (hrs.) | Remarks |
|---|---|---|---|---|---|---|
| T-1 | 100 | 0 | 0 | same composition as that of matrix | 100 | Outside the scope of this invention |
| T-2 | 80 | 0 | 20 | same composition as that of matrix | 250 | Outside the scope of this invention |
| T-3 | 20 | 40 | 40 | same composition as that of matrix | 330 | Outside the scope of this invention |
| T-4 | 50 | 0 | 50 | same composition as that of matrix | 350 | Within the scope of this invention |
| T-5 | 20 | 30 | 50 | same composition as that of matrix | 360 | Within the scope of this invention |
| T-6 | 30 | 10 | 60 | same composition as that of matrix | more than 500 | Within the scope of this invention |
| T-7 | 20 | 4 | 76 | same composition as that of matrix | more than 500 | Within the scope of this invention |
| T-8 | 15 | 0 | 85 | same composition as that of matrix | 400 | Within the scope of this invention |
| T-9 | 15 | 0 | 85 | same composition as that of matrix + $Al_2O_3$ (5 wt %) | more than 500 | Within the scope of this invention |
| T-10 | 15 | 0 | 85 | same composition as that of matrix + $SiO_2$ (2 wt %) | more than 500 | Within the scope of this invention |
| T-11 | 10 | 0 | 90 | same composition as that of matrix + $Fe_2O_3$ (5 wt %) | more than 500 | Within the scope of this invention |
| T-12 | 0 | 0 | 100 | same composition as that of matrix | 100 | Outside the scope of this invention |

It can be seen from the above Table 1 that when electrode-adhering particles having a composition within the scope of the present invention are used, the resulting oxygen concentration cell has a duration time of as long as more than 350 hours. While, conventional oxygen concentration cells have a duration time of less than 250 hours. Therefore, it has been found that the oxygen concentration cell according to the present invention is superior by 40% in the peeling resistance of electrode to the conventional oxygen concentration cells.

What is claimed is:

1. A method for producing an oxygen concentration cell suitable for exposure to high temperature combustion gases which comprises the steps of:
    (a) forming a green matrix by press molding a stabilized or partially stabilized zirconia raw material powder;
    (b) producing electrode-adhering particles made of stabilized or partially stabilized zirconia granulated particles which have a substantially spherical shape and which contain no less than fifty percent by weight of granulated particles having a size of at least 44 microns and no less than ten percent by weight of fine particles having a size of no greater than ten microns to act as a sintering aid, said electrode-adhering particles being produced through granulation by spray drying fine primary particles;
    (c) preparing fluidized electrode-adhering particles by adding an organic binder to said electrode-adhering particles;
    (d) applying said fluidized electrode-adhering particles to a surface of said green matrix;
    (e) sintering the green matrix and the applied electrode-adhering particles to form a monolithic matrix having a plurality of convex portions on the surface of the sintered matrix;
    (f) applying an electrode to the surface of the sintered matrix; and
    (g) applying a heat-resistant ceramic protective film to the electrode.

2. The method of claim 1 in which said granulated particles have an average particle size of 50 to 100 μm.

3. The method of claim 1 in which the raw material powder of the press-molded matrix, the primary particles of the granulated particles and the fine particles of the sintering aid are all fine particles having a particle size of not larger than 10 μm and in which the electrode-adhering particles produced therefrom contain not less than 60% by weight of the granulated particles having a size not smaller than 44 μm.

4. The method of claim 1 in which the granulated particles are applied and adhered to the press-molded matrix surface in the form of one or several layers.

5. The method of claim 1 in which the granulated particles are first adhered to the press-molded matrix surface and then the fine particles are adhered to a film of the granulated particles to form a film of the electrode-adhering particles on the matrix surface.

6. The method of claim 1 in which the granulated particles are produced by granulating a raw material mixture of stabilized or partially stabilized zirconia raw material powders having up to 5% by weight of a sintering aid based on the amount of the zirconia raw material powders.

* * * * *